(12) United States Patent
Viquez et al.

(10) Patent No.: US 11,672,565 B2
(45) Date of Patent: *Jun. 13, 2023

(54) INTRODUCER DEVICES AND METHODS OF USE THEREOF

(71) Applicant: ESTABLISHMENT LABS S.A., Alajuela (CR)

(72) Inventors: Jose Pablo Viquez, Alajuela (CR); Eckart Holst, Alajuela (CR); Solange Vindas, Alajuela (CR); Ariel Seidner H., Alajuela (CR); Matthew Solar, Melbourne, FL (US); Roberto De Mezerville, Alajuela (CR); Juan José Chacón Quirós, Alajuela (CR); Thomas Fuller, Alajuela (CR); Nathalia Araujo, Alajuela (CR)

(73) Assignee: Establishment Labs S.A., Alajuela (CR)

( * ) Notice: Subject to any disclaimer, the term of this patent is extended or adjusted under 35 U.S.C. 154(b) by 0 days.

This patent is subject to a terminal disclaimer.

(21) Appl. No.: 17/749,635

(22) Filed: May 20, 2022

(65) Prior Publication Data
US 2022/0280190 A1 Sep. 8, 2022

Related U.S. Application Data

(63) Continuation of application No. 17/282,403, filed as application No. PCT/IB2019/058401 on Oct. 2, 2019.
(Continued)

(51) Int. Cl.
*A61F 2/12* (2006.01)
*A61B 17/34* (2006.01)
*A61B 17/00* (2006.01)

(52) U.S. Cl.
CPC ............ *A61B 17/3468* (2013.01); *A61F 2/12* (2013.01); *A61B 2017/00535* (2013.01); *A61B 2017/00792* (2013.01); *A61B 2017/00796* (2013.01)

(58) Field of Classification Search
CPC ...... A61B 17/3468; A61B 2017/00535; A61B 2017/00792; A61B 2017/00796; A61F 2/12
(Continued)

(56) References Cited

U.S. PATENT DOCUMENTS 10,398,543 B1 * 9/2019 Solar .................. A61B 17/3468
10,905,466 B2 * 2/2021 Chacon Quiros ... A61M 5/2053
(Continued)

FOREIGN PATENT DOCUMENTS

BR 112021006126 7/2021
CA 3115037 4/2020
(Continued)

OTHER PUBLICATIONS

"Israel Application Serial No. 281866, Notification Prior to Examination dated Oct. 17, 2021", w o English Translation, 2 pgs.
(Continued)

*Primary Examiner* — Suzette J Gherbi
(74) *Attorney, Agent, or Firm* — Schwegman Lundberg & Woessner, P.A.

(57) ABSTRACT

Aspects of the present disclosure are directed to a medical implant introducer (100) and methods of its use. The introducer (100) may include a handle (120), an implant-holding cavity disposed distally from the handle (120), a fluid supply conduit (122) fluidly coupled to an interior portion of the implant-holding cavity, and a distal nozzle (110) having a proximal portion, a distal portion, a middle portion in between the proximal portion and the distal portion, the
(Continued)

middle portion having a tapered profile such that the proximal portion is larger than the distal portion, and a distal opening (112), wherein an implant in the implant-holding cavity may be expelled from the introducer (100) through the distal opening (112).

26 Claims, 13 Drawing Sheets

Related U.S. Application Data

(60) Provisional application No. 62/740,693, filed on Oct. 3, 2018.

(58) Field of Classification Search
USPC .......................................................... 623/7–8
See application file for complete search history.

(56) References Cited

U.S. PATENT DOCUMENTS

| | | | |
|---|---|---|---|
| 10,952,773 B2* | 3/2021 | Carson | A61K 31/573 |
| 11,337,725 B2* | 5/2022 | Clark, III | A61B 17/32 |
| 2006/0224144 A1 | 10/2006 | Lee | |
| 2009/0177165 A1 | 7/2009 | Tsao | |
| 2015/0126812 A1 | 5/2015 | Anderson | |
| 2020/0163543 A1* | 5/2020 | Schutt | A61B 17/00234 |
| 2021/0169666 A1* | 6/2021 | Winn | A61F 2/12 |
| 2021/0338280 A1* | 11/2021 | Viquez | A61F 2/12 |
| 2022/0160491 A1* | 5/2022 | Zemmel | A61F 2/0095 |
| 2022/0168014 A1* | 6/2022 | Dale | A61B 17/00234 |

FOREIGN PATENT DOCUMENTS

| | | |
|---|---|---|
| CN | 204033389 | 12/2014 |
| CN | 113164189 | 7/2021 |
| EP | 3087951 | 11/2016 |
| EP | 3860478 | 8/2021 |
| HK | 40059340 A | 5/2022 |
| HK | 40059343 A | 5/2022 |
| IL | 281866 | 5/2021 |
| KR | 20210075105 | 6/2021 |
| WO | 2017181144 | 10/2017 |
| WO | 2020070676 | 4/2020 |

OTHER PUBLICATIONS

"International Application Serial No. PCT IB2019 058401, International Search Report dated Dec. 3, 2019", 6 pgs.

"U.S. Appl. No. 17 282,403, Preliminary Amendment filed Apr. 2, 2021", 3 pgs.

"U.S. Appl. No. 17 282,403, Supplemental preliminary amendment filed Oct. 28, 2021", 7 pgs.

"International Application Serial No. PCT IB2019 058401, Written Opinion dated Dec. 3, 2019", 8 pgs.

"International Application Serial No. PCT IB2019 058401, International Preliminary Report on Patentability dated Apr. 15, 2021", 10 pgs.

"European Application Serial No. 19783724.8, Response to Communication pursuant to Rules 161(1) and 162 EPC filed Nov. 22, 2021", 14 pgs.

* cited by examiner

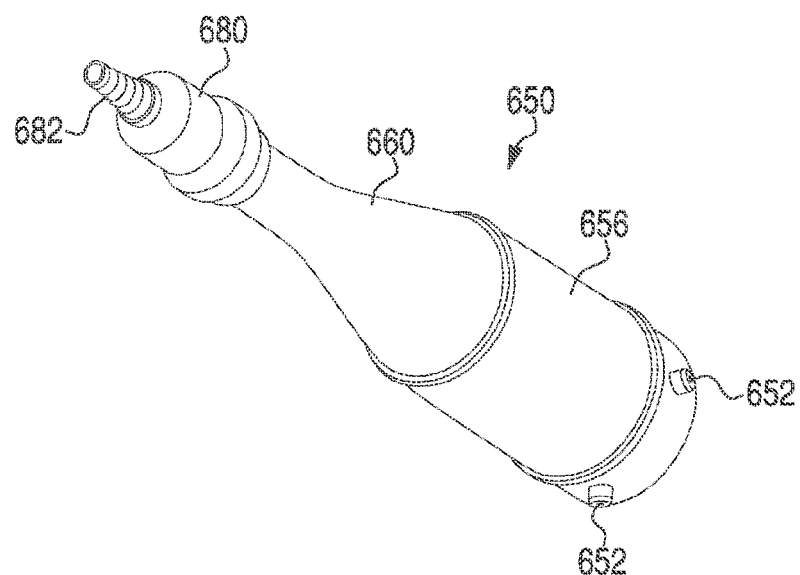
FIG. 14D
FIG. 15
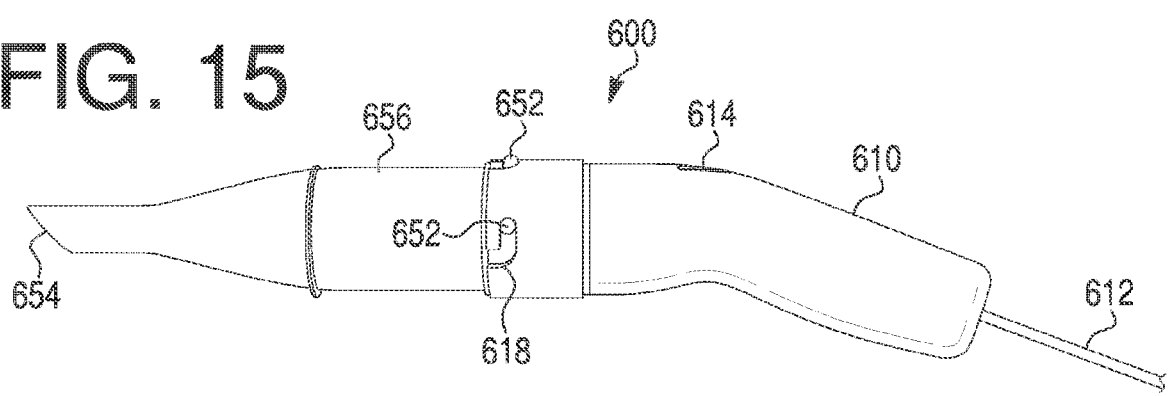

INTRODUCER DEVICES AND METHODS OF USE THEREOF

CROSS-REFERENCE TO RELATED APPLICATIONS

This application is a continuation of U.S. patent application Ser. No. 17/282,403, filed on Apr. 2, 2021, which is the U.S. national phase entry under 35 U.S.C. 0 371 of International Application No. PCT/IB2019/058401, filed on Oct. 2, 2019, which claims priority to U.S. Provisional Application No. 62/740,693, filed on Oct. 3, 2018, which is incorporated by reference herein in its entirety.

TECHNICAL FIELD

The present disclosure relates generally to prosthetic implant introduction devices and methods of use thereof.

BACKGROUND

Current techniques for insertion of medical implants, such as breast implants, may create surgical wounds resulting in an extended, complex, and/or dynamic healing process. e.g., to allow a patient body to replace devitalized and missing cellular structures and/or tissue layers. For example, many current techniques require a relatively large incision at or near a surgical implantation site (e.g., a tissue pocket). The incision may need to be manipulated by retractors and/or tissue-spreaders to expand and hold it open, while an implant is physically manipulated into the implantation site. These techniques may result in heavy scarring, a high probability of damage to the implant, and/or a high probability of infection at the implantation site. Moreover, these techniques may require insertion of drainage tubes to evacuate serous fluids from surrounding tissue and prevent capillary damage; and/or may accelerate inflammatory responses that impact the healing process. In addition, it is recognized that the larger the incision, the greater potential incidence for keloid and hypertrophic scarring during and after healing. Certain patients are also more susceptible to, and are at higher risk of, keloid formation.

SUMMARY

Aspects of the present disclosure are directed to an implant introducer, including: a handle including a conduit configured to receive a pressurized fluid, and a nozzle coupled to, and detachable from, the handle. The nozzle may have a proximal portion and a distal portion that includes a distal opening, the nozzle having a tapered profile such that a cross-sectional dimension of the proximal portion is larger than a cross-sectional dimension of the distal portion. The introducer may include a cavity distal to the handle, and may be configured to expel an implant housed within the cavity through the distal opening via fluid pressure through the conduit.

Optionally, the nozzle includes the cavity. Additionally or alternately, the proximal portion of the nozzle includes mating features complementary to mating features of a distal portion of the handle. Optionally, one of the handle or the nozzle includes protrusions, and the other of the handle of the nozzle includes channels configured to receive the protrusions; or, the handle and the nozzle include complementary threaded portions. Optionally, the introducer includes a middle portion between the handle and the nozzle, and the middle portion includes the cavity. Optionally, the distal opening of the nozzle has a cross-sectional dimension ranging from about 20 mm to about 40 mm, such as from about 25 mm to about 30 mm. Optionally, the handle includes an actuator configured to control a flow of pressurized fluid distally through the conduit to the cavity. Optionally, the actuator includes a valve configured to control a fluid pressure of about 20 psi to about 100 psi through the conduit. Optionally, the introducer includes a chamber disposed within the cavity, the chamber being in communication with the conduit and configured to expand upon a flow of fluid into the chamber.

Optionally, the handle includes a vent configured to selectively vent pressurized fluid from the chamber. Optionally, the introducer further comprises a cap covering the distal opening of the nozzle, the cap being removable from the distal opening and including an aperture in communication with the distal opening. Optionally, the cap is configured to form a fluid-tight seal with the nozzle. Optionally, the distal portion of the nozzle is more flexible than the proximal portion of the nozzle, and optionally the distal portion of the nozzle includes a plurality of flexible strips. Optionally, the nozzle includes an extension adjacent to the distal opening, the nozzle having an asymmetrical shape. Optionally, the nozzle is configured to compress an elastic implant, such as a breast implant.

Aspects of the present disclosure are also directed to an implant introducer, comprising a handle including a conduit, and a nozzle coupled to, and detachable from, the handle via complementary mating features, the nozzle having a proximal portion and a distal portion that includes a distal opening, wherein the nozzle has a tapered profile such that a cross-sectional dimension of the proximal portion is larger than a cross-sectional dimension of the distal opening. The conduit may be in fluid communication with the nozzle, and the introducer includes a cavity distal to the handle, the introducer being configured to expel an implant housed within the cavity through the distal opening via fluid pressure through the conduit.

Optionally, the nozzle includes the cavity. Optionally, the introducer further includes a cap configured to form a fluid seal with the nozzle, the cap being removable from the nozzle, wherein the cap includes an opening to apply vacuum pressure to the nozzle. Optionally, the nozzle includes a plurality of flexible strips surrounding the distal opening. Optionally, the nozzle includes an extension adjacent to the distal opening. Optionally, the distal opening has an oval shape, a maximum diameter of the distal opening ranging from about 25 mm to about 35 mm.

Aspects of the present disclosure are directed to an implant introducer, including: a handle including an actuator; a nozzle coupled to, and detachable from, the handle, the nozzle having a proximal portion that includes a cavity and a distal portion that includes a distal opening in communication with the cavity, wherein a diameter of the cavity is greater than a diameter of the distal opening, and wherein the distal portion is more flexible than the proximal portion; and a conduit fluidly coupled to a chamber defined by a membrane, the chamber configured to expand at least partly in the cavity upon a flow of fluid into the chamber controlled by the actuator. Optionally, a breast implant is disposed in the cavity. Optionally, the breast implant includes a flexible shell and a visco-clastic filling gel.

Further aspects of the present disclosure are directed to a method for loading an implant into an introducer that includes a nozzle and a handle. The method may include inserting the implant into a cavity of the nozzle, the nozzle having a proximal portion that includes the cavity and a distal end portion that includes a distal opening, wherein the cavity has a diameter greater than a diameter of the distal opening, and attaching the proximal portion of the nozzle to the handle. The handle may include a conduit configured to receive pressurized fluid and supply the pressurized fluid to the nozzle. Optionally, inserting the implant into the cavity includes drawing the implant into the cavity by vacuum pressure. Optionally, the method may further include ejecting the implant from the introducer by pushing the implant through the distal opening of the nozzle via fluid pressure supplied through the conduit.

BRIEF DESCRIPTION OF THE DRAWINGS

Embodiments of the present disclosure may be implemented in connection with aspects illustrated in the attached drawings. These drawings show different aspects of the present disclosure and, where appropriate, reference numerals illustrating like structures, components, materials, and/or elements in different figures are labeled similarly. It is understood that various combinations of the structures, components, and/or elements, other than those specifically shown, are contemplated and are within the scope of the present disclosure. Further, even if it is not specifically mentioned, aspects described with reference to one embodiment may also be applicable to, and may be used with, other embodiments.

Moreover, the present disclosure is neither limited to any single aspect or embodiment, nor to any combinations and/or permutations of such aspects and/or embodiments. Each aspect of the present disclosure (e.g., device, method, etc.) and/or variations thereof, may be employed alone or in combination with one or more of the other aspects of the present disclosure and/or variations thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations. Rather, it is intended to reflect or indicate the embodiment(s) is/are "example" embodiment(s).

FIGS. 14A-14D show various views of a nozzle and cap assembly of an introducer, according to some aspects of the present disclosure.

FIG. 15 shows a side view of an assembled introducer, according to some aspects of the present disclosure.

DETAILED DESCRIPTION

Figure 1:
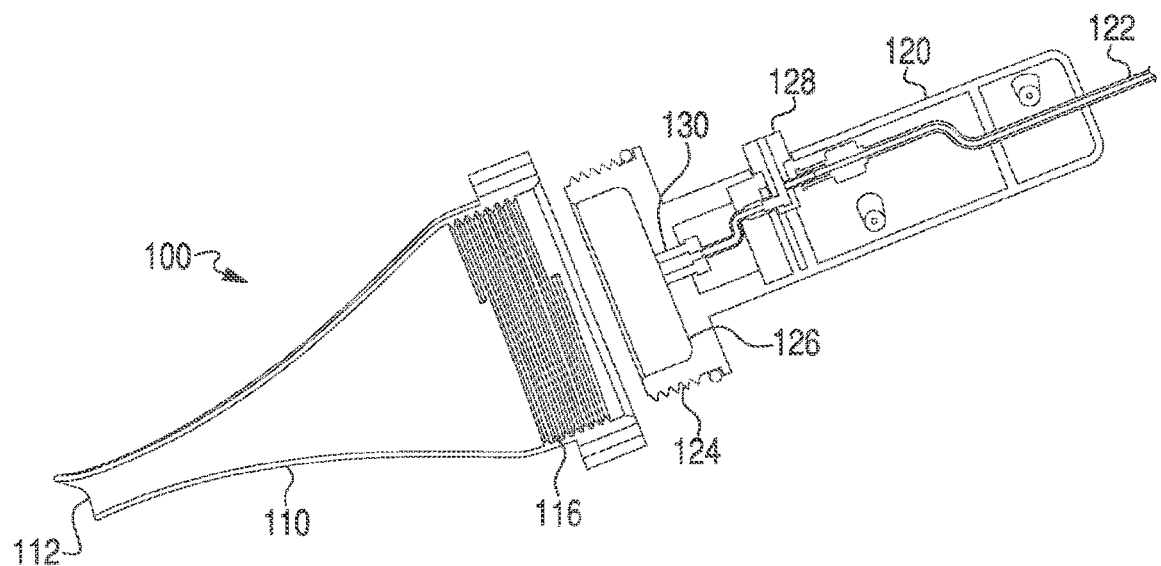
FIGS. 1 and 2 show views of an introducer (implant introduction device), according to some aspects of the present disclosure.

Examples of the present disclosure relate to systems, devices, and methods for treating internal areas of a patient's body. Such systems, devices, and methods may include an introducer (also referred to herein as an introducer device) and an implant (e.g., a prosthesis for introduction into the body) of a patient.

The terms and definitions provided herein control, if in conflict with terms and/or definitions of art or those incorporated by reference. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

The terms "proximal" and "distal" are used herein to refer to the relative and directional positions of the components of an exemplary introducer device. "Proximal" or "proximally" refers to a position relatively closer to an operator of a device. In contrast, "distal" or "distally" refers to a position relatively farther away from the operator of a device, and or closer to an interior of a patient body.

Disclosed herein are instruments, devices (introducers, e.g., implantation or introducer devices), systems, and methods useful for the introduction of an implant, such as a prosthetic implant, into an implantation site. In some embodiments, devices, systems, and methods disclosed herein may provide for introduction of an implant into an implantation site in a minimally-invasive manner (e.g., in a manner intended to reduce the extent, size, and/or shape of incisions and/or tissue displacements at or near an implantation site). For example, the introducer devices described herein may be used to deliver implants via one or more minimally invasive procedures. In some cases, devices, systems, and methods disclosed herein may provide for introduction of an implant into an implantation site in a non-minimally-invasive procedure.

Implants according to the present disclosure may include, e.g., breast, gluteal, calf, and other medical implants, including aesthetic and/or reconstructive implants. Suitably, implants according to the present disclosure may be partly or entirely flexible (e.g., elastomeric, compressible, expandable, and/or resiliently deformable). In at least one example, an implant for use with the instruments, devices, systems, and methods disclosed herein may be a breast implant with elastic properties, e.g., super visco-elastic and/or highly elastic properties. According to some aspects of the present disclosure, the implant may comprise a fluid, such as a liquid or gel, including viscous gels. For example, the implant may comprise silicone filling gel, wherein the implant may be pre-filled with the silicone gel prior to, or after, implantation. The implant may comprise a shell (e.g., an outer casing) with biocompatible surfaces. For example, the implant may have a surface texture as disclosed in one or more of WO 2015/121686, WO 2017/093528, and/or WO 2017/196973. In some aspects, the shell may have a combination of surface features or characteristics, such as, e.g., roughness, kurtosis (e.g., referring to the distribution of peak heights and valley depths of the surface), and/or skewness of the surface that provide for a surface texture with increased biocompatibility. The shell may have low-friction surface properties to facilitate smooth delivery and implantation of the implant within the body of the patient. While references to breast implants are used throughout the remainder of this disclosure, the disclosure is not so limited. Rather, the systems, devices, and methods disclosed herein may be used to deliver any suitable implants. e.g., aesthetic implants and/or implants used in reconstructive medical procedures. For example, the systems, device, and methods herein may be used to deliver one or more of breast, gluteal, calf, and/or other implants into the body of the patient.

Aspects of the introducer devices, systems, and methods of the present disclosure may be used in combination with the devices and methods disclosed in WO 2017/181144, incorporated by reference herein.

The introducer devices described herein may be used to standardize and/or facilitate procedures for implantation of a breast implant or other implant device. In some examples, an introducer device may be configured for one-handed advancement of the implant into an implantation site. In some aspects, a combination of features of the implant and the introducer system may facilitate a minimally-invasive procedure, e.g., to improve patient well-being. For example, a breast implant characterized by elastic properties (such as, e.g., a combination of high shell elongation, high shell strength, and visco-elastic filling gel), optionally with surface texturing, may be implanted with an introducer device as described herein in a minimally-invasive insertion method to minimize scarring of the incision site, reduce the risk of damaging the implant during placement, and/or to accelerate and optimize healing of the surgical wound. Optionally, an introducer device as described herein may have surface friction properties to facilitate smooth delivery and implantation of the implant within the body of the patient. In some arrangements, the introducer devices described herein may adapt to a sterile packaging system to provide a "touchless" implantation procedure. That is, a physician, nurse, or other medical professional or user need not directly handle an implant when loading the implant into an introducer device or at other times during implantation. For example, the implant may be pre-packaged inside the nozzle in a sterile manner, such that the medical professional need not touch the implant during the procedure.

Reference will now be made to the figures of the present disclosure.

Figure 2:
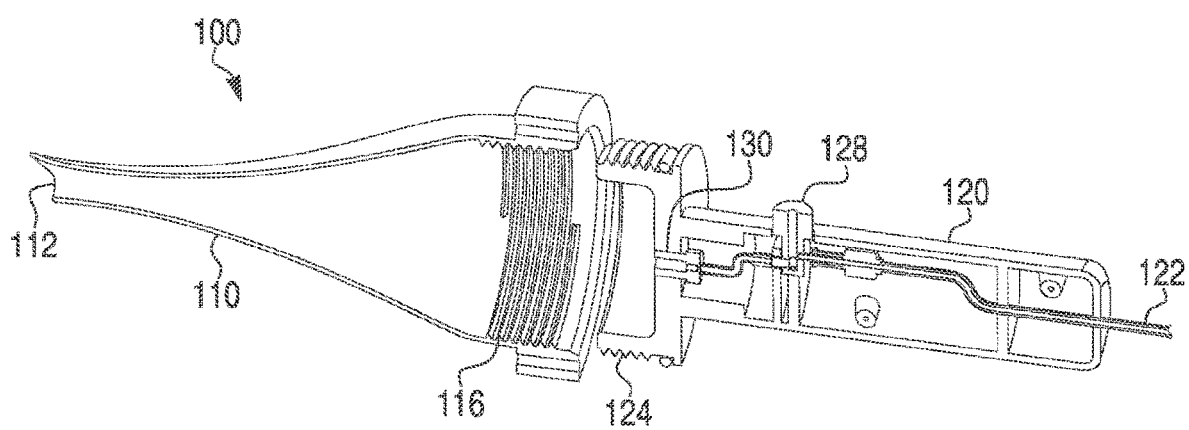

FIGS. 1 and 2 illustrate an exemplary introducer 100, which may be used for delivery of an implant into an implantation site. Introducer 100 may include a nozzle 110 and a handle 120. Nozzle 110 may include a distal opening 112 and an engagement area 116 for engaging with a complementary engagement area 124 of handle 120. Handle 120 may further include a fluid supply conduit or lumen 122, a stopper 126, an actuator 128, and a fluid supply mouth 130.

Figure 3:
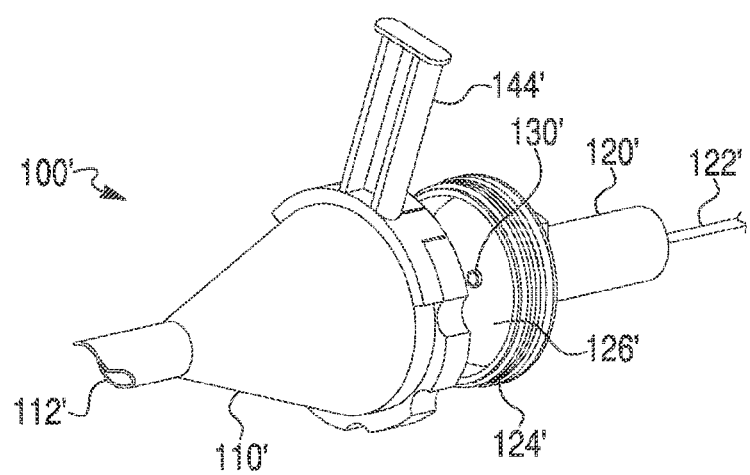
FIG. 3 shows a view of a variation on an introducer, according to some aspects of the present disclosure.

Introducer 100 may have any of a variety of suitable sizes, shapes, and characteristics suitable for holding and delivering an implant. Generally, introducer 100 may include, e.g., nozzle 110 and handle 120, where each of nozzle 110 and handle 120 may have any one of various shapes and sizes. While FIGS. 1 and 2 depict one variation of introducer 100 according to the present disclosure, FIG. 3 depicts an additional variation (introducer 100'). Further, FIGS. 13-17 and FIG. 18 depict additional variations of an introducer (introducers 600, 700) which may share any of the characteristics (e.g., nozzle characteristics, handle characteristics, reusability, identifying characteristics, interchangeability etc.) described herein with respect to introducer 100 and/or 100'. Additionally. FIGS. 4A-12D depict exemplary nozzle sizes and shapes which may be applicable in combination with any of the introducers disclosed herein.

Introducer 100 and/or an implant for use with introducer 100 may include identifying characteristics, such as a unique device identifier (UDI) with information useful for identifying the introducer device or implant. For example, the UDI may include a micro-transponder for identification of introducer 100, and/or in an implant for post-implantation implant recognition and traceability. In some aspects, introducer 100 and/or an implant for use with introducer 100 may, include one or more sensors with the ability to measure temperature, change in electrical impedance, and/or pressure, e.g., to be used as a control signal to alert or diagnose shell rupture, infection of the patient's tissue, and/or signs of an inflammatory response of the patient's tissue by monitoring the surrounding tissue temperature. Such one or more sensors may be a part of or separate from a UDI. Such UDI and/or sensor(s) may be placed in any suitable position on or within introducer 100 or the implant, including, for example, an inner surface of introducer 100 proximate and/or in contact with the implant.

In some embodiments, introducer 100 may be a single-use (e.g., disposable) device. In further embodiments, some or all of introducer 100 (e.g., handle 120 and/or nozzle 110) may be reusable, such as after sterilization.

Referring now to further characteristics of introducer 100, nozzle 110 may define a cavity for housing an implant pre-implantation. In some embodiments, a cavity defined by nozzle 110 may be configured to house an implant in a compressed, rolled, or otherwise reduced-size configuration. In such embodiments, a diameter or cross-sectional dimension of nozzle 110 may define the cross-sectional size of the implant in the compressed/rolled etc. configuration. The dimensions of nozzle 110 may be selected based on the dimensions (e.g., size and shape) of the implant to be delivered using introducer 100, and/or vice-versa (e.g., characteristics of the implant may be selected based on the dimensions of nozzle 110).

Nozzle 110 may have any configuration suitable for inserting an implant through an incision, e.g., as described herein and/or in WO 2017/181144, incorporated by reference herein. Nozzle 110 may have a portion having tapered profile, such that it has a larger diameter or cross-sectional dimension at its proximal end portion than the diameter or cross-sectional dimension at its distal end portion. Additionally, nozzle 110 may have a proximal end portion for coupling with, e.g., handle 120, and a distal opening 112. In some embodiments, a portion of nozzle 110 having a tapered profile may include the majority of nozzle 110. In other embodiments, a relatively smaller percentage of nozzle 110 may include a tapered profile (e.g., less than about 50%, less than about 40%, less than about 30%, or less than about 25% of nozzle 110 may have a tapered profile).

Nozzle 110 may be a single piece, or may comprise multiple pieces that are fitted, slotted, assembled, clipped, welded, or otherwise joined together at one or more joining points. Nozzle 110 also may have additional profiles and features (e.g., with respect to a cavity for housing an implant and/or with respect to distal opening 112), as described further herein. Nozzle 110 may be formed from or may otherwise comprise one or more biocompatible polymer or copolymer material(s) (e.g., polyurethane, polyethylene, silicone, polycarbonate, a combination thereof, etc.). Nozzle 110 may be rigid, semi-rigid, flexible or a combination thereof. For example, distal opening 112 of nozzle 110 may be rigid enough to dilate an incision site on a patient and direct an implant to the incision site, but soft enough to avoid tearing or damaging the site and/or to avoid deformation of the implant. Moreover, distal opening 112 may be more flexible than, e.g., a proximal end portion of nozzle 110, which may be mom rigid to facilitate engagement with handle 120. In some embodiments, nozzle 110 may be disposable.

As described elsewhere herein, implants suitable for use with, e.g., introducer 100 may be moldable, pliant, compressible, and/or otherwise movable between a compressed, insertion configuration and a deployed, expanded configuration. For example, an implant for use with introducer 100 may comprise a high-strength flexible shell with viscoelastic and low friction surface properties. As mentioned, nozzle 110 may define a chamber to receive an implant in an insertion configuration (e.g., a fully or partially compressed, folded, rolled, or any other low-profile configuration). Following delivery out of distal opening 112 and into the body of a patient, the implant may expand, decompress, or otherwise assume a deployed configuration.

Any one or more portions of nozzle 110, such as an inner surface of nozzle 110, may include a lubricious coating to reduce the coefficient of friction between one or more portions (e.g., the inner surface) of introducer 100 and one or more portions of an implant housed within. For example, a lubricious coating may be a water-activated coating fixed on one or more surfaces of nozzle 110, such as an interior surface. Additionally or alternately, a lubricious coating may include a biocompatible lubricant and/or any other biocompatible coating. The coating may reduce a coefficient of friction between the implant shell and the interior surface of nozzle 110, promoting a smooth transition between the insertion configuration and the deployed configuration of the implant, e.g., upon exit of the implant from introducer 100.

Some aspects of nozzle 110 may be designed to reduce the risk of tearing or other damage to an implant or patient tissue. In some aspects, characteristics of nozzle 110 may be designed to aid in achieving a desired expulsion pressure against an implant when introducer 100 is actuated to deposit the implant, and/or may aid in achieving a desired ejection speed of an implant through the distal end of nozzle 110. In some embodiments, characteristics of, e.g., distal opening 112 may be designed or selected to achieve a desired implant ejection speed or implant ejection pressure, or may be designed or selected to improve placement precision of introducer 100, biocompatibility of introducer 100 with patient tissue, compatibility with a particular incision size, and/or other goals.

Distal opening 112 may be an aperture at or near a distal portion of nozzle 110 through which an implant housed in a cavity of introducer 100 (e.g., inside nozzle 110) may exit introducer 100 during an implantation procedure. In some embodiments, distal opening 112 may be at a distal-most end of nozzle 110. Distal opening 112 may be a distally-facing opening, and/or may be angled with respect to a proximal-distal axis of nozzle 110. A cross-sectional size of distal opening 112 (e.g., a diameter of distal opening 112) may have any suitable size, e.g., to achieve one or more of the objectives above. In some embodiments, a cross-sectional size of distal opening 112 may range from about 0.5 cm to about 5 cm, such as from about 0.5 cm to about 3.5 cm, from about 1 cm to about 3 cm, from about 1 cm to about 2 cm, or from about 1.5 cm to about 2.5 cm.

In some examples, at least a portion of nozzle 110, such as a perimeter of distal opening 112, may be configured to flex, e.g., as the implant passes through the distal opening of the nozzle, such that the cross-sectional size of distal opening 112 may increase as an implant passes therethrough (e.g., increasing from about 0.5 cm to about 2 cm, to about 2.5 cm, to about 3 cm, or to about 3.5 cm).

Distal opening 112 may have any suitable shape, such as, e.g., round, oval, half-oval (e.g., having one side that is flat and another side that is rounded or oval), otherwise curved, or angular in shape. The size and shape of distal opening 112 may be selected to accommodate the size and shape of the implant to be introduced into a patient, to guide the implant through an incision into an implantation site, and/or to facilitate introduction of a distal portion of nozzle 110 through an incision. For example, distal opening 112 may have a half-oval or angular shape to accommodate a non-round implant. An angling of distal opening 112, and/or diameter of distal opening 112, may also be customized. Moreover, distal opening 112 may be bordered, flanked, and/or defined by one or more slits, flaps, petals or extensions disposed about a perimeter of distal opening 112. Such features may be disposed in a circumferential arrangement about distal opening 112, or may be disposed symmetrically or asymmetrically about distal opening 112. In some embodiments, such features may assist in positioning distal opening 112 through an incision and/or guiding placement of an implant through distal opening 112 into an implantation site. In some embodiments, such features may be flexible (e.g., flexible enough to bend upon pressure being exerted on them by the passage of an implant, or, in some embodiments, more flexible than a proximal region of nozzle 110). The present disclosure includes multiple exemplary variations of distal openings on nozzles, any of which may be used in combination with nozzle 110 of introducer 100, or with any other introducer described or encompassed by this disclosure. It will be apparent to those of skill in the art that variations upon each of these exemplary nozzles are contemplated as well.

Other characteristics of nozzle 110 may be selected so as to accommodate differently sized and shaped implants, and/or to provide a desired flexibility, expulsion pressure, and/or other characteristic to introducer 100. For example, a degree or angle of taper, a taper shape, and/or a length of nozzle 110 may be selected so as to accommodate differently sized and shaped implants and/or to facilitate guidance of a portion of nozzle 110 through an incision and/or placement of an implant in an implantation site. In some embodiments, nozzle 110 may include a flared shape (e.g., at a distal portion of nozzle 110), which may aid in insertion of nozzle 110 into an incision and/or safe and effective deployment of an implant.

Handle 120 may be coupleable, either reversibly or permanently, to nozzle 110. Handle 120 may include a body that houses fluid supply lumen 122. A shape and size of handle 120 may be configured for ease of use by an individual. In some embodiments, handle 120 may be grippable by one hand, to allow for a user to manipulate introducer 100 one-handed.

Handle 120 may be configured to be attached, detached and/or reattached to nozzle 110 via a suitable mechanism, which may include engagement surface 124 of handle 120 and/or engagement surface 116 of nozzle 110. Exemplary attachment mechanisms include, but are not limited to, threads, clamps, screws, and tabs, which may be disposed at, on, and/or around contacting portions of handle 120 and/or nozzle 110. In some embodiments, as shown in FIGS. 1 and 2, engagement surface 124 may include a plurality of threads complementary to a plurality of threads of engagement surface 116. In further embodiments, engagement surfaces 124, 116 may include other mating features (e.g., clips, clamps, adhesive, etc.) to facilitate attachment of handle 120 to nozzle 110 either permanently or reversibly.

Handle 120 may define or encompass fluid supply lumen 122, which may be configured for the passage of a fluid, e.g., from a source of fluid (not shown) to which it is connected, through handle 120 and fluid supply mouth 130 to an interior portion of nozzle 110. Fluid supply lumen 122 may be coupled or coupleable to a fluid supply via any suitable connection, such as, but not limited to, a Luer connection, threaded connection, clip connection, lock connection, etc. The fluid supply may include a pressurized fluid source, such as a pressurized gas or liquid. In some embodiments, the pressurized fluid source may include, e.g., a portable compressed fluid canister, a pressurized fluid line (e.g., a gas line or water line), or the like. In some embodiments, for example, the fluid source may be a disposable or refillable canister of compressed gas. An implant loaded into introducer 100 may be installed such that fluid supply lumen 122 and fluid supply mouth 130 may be positioned to deliver pressurized fluid to a region located proximally from the implant. Such pressurized fluid, when delivered, may impart pressure on the implant to drive the implant distally towards and through distal opening 112 of nozzle 110. In some embodiments, as discussed elsewhere herein, fluid supply lumen 122 and fluid supply mouth 130 may be configured to conduct pressurized fluid from a fluid supply into an expandable cavity, such as a balloon, expandable chamber, or cavity defined by a membrane, disposed at least partially within a proximal region of nozzle 110. Pressure from pressurized fluid into such an expandable cavity may expand the cavity and/or move a membrane, balloon wall, or cavity wall to impart pressure on an implant and drive it distally, through distal opening 112. As described elsewhere herein (e.g., with respect to introducers 600, 700), handle 120 may further include an openable vent between the expandable cavity and an exterior of the introducer, to allow for venting of pressurized fluid from the expandable cavity.

Handle 120 may include a stopper 126, e.g., defined by a distal end or distal-facing wall of handle 120. Stopper 126 may be sized and configured to cover and/or close a proximal end of nozzle 110. In some embodiments, when handle 120 is coupled to nozzle 110, stopper 126 may define a proximal-most wall of a cavity that may house an implant in introducer 100. In at least one example, stopper 126 is configured to seal the proximal end of nozzle 110 after an implant has been positioned in the cavity. Stopper 126 may be held in place against nozzle 110 by connection or mating features that may attach handle 120 to nozzle 110, such as, e.g., engagement surfaces 124, 116, which may include threads, a Luer-type connection, an adhesive, a vacuum- or suction-type closure, clips, clamps, etc. In some embodiments, stopper 126 may include an elastomeric surface, e.g., to better form a seal against nozzle 110. Fluid supply mouth 130 may pass through stopper 126 (as shown in FIG. 1), to allow for delivery of pressurized fluid to a cavity distal to stopper 126.

Handle 120 may include actuator 128 for selectively supplying and terminating the flow of compressed gas or other pressurized fluid from the fluid supply through fluid supply mouth 130. Actuator 128 may include, e.g., a button, knob, valve, switch, clip, or combinations thereof, which may open/create and/or close a connection between a more proximal portion of fluid supply lumen 122 and fluid supply mouth 130. In some embodiments, actuator 128 may be spring-loaded or otherwise may employ consistent pressure to maintain an open flow of pressurized fluid towards an implant housed in a cavity of nozzle 110.

FIG. 3 depicts an introducer 100', similar to introducer 100. Introducer 100' includes a nozzle 110' having a distal opening 112', and a handle 120' having fluid supply lumen 122', stopper 126', and engagement area 124'. Aspects of introducer 100' may share any characteristics with like aspects of introducer 100. As shown, nozzle 110' includes a conical tapered portion and a distal tip (including distal opening 112') forming an angle with the conical tapered portion. Introducer 100' further includes a holding attachment 144' attached to a proximal portion of nozzle 110'. Holding attachment 144' may aid in. e.g., manipulation of introducer 100'. This may reduce or remove the need to touch nozzle 110', which may aid in, e.g., maintaining cleanliness and/or sterility of nozzle 110' and/or of a user's hand prior to or during a surgical procedure. In some embodiments, holding attachment 144' may aid in loading an implant into nozzle 110'. Holding attachment 144' may be attachable to, e.g., nozzle 110' or handle 120' by any suitable means, such as complementary threads, a clip, a snap-on connection, adhesive, etc.

As mentioned above, introducers described herein (e.g., introducer 100 described above, and/or introducers 600, 700, or variations thereof) may be used for implantation of an implant with visco-elastic and/or other elastic properties, e.g., the implant comprising an elastic shell and viscoelastic filling gel. Such elastic properties of the implant facilitate manipulation of the implant. e.g., allowing the implant to be compressed, stretched, and/or elongated for loading into a nozzle (e.g., nozzle 110) of an introducer (e.g., introducer 100) in a reduced profile, for implantation in a manner which may reduce trauma to a patient. In some embodiments, such implantation may be part of a minimally-invasive procedure. Various properties of introducer 100 and/or the implant may allow for radial compression of the implant, which may provide an ability to safely compress the implant for advancement into a smaller incision. For example, various properties of introducer 100 may be sized and configured to assist in compressing the implant for advancement into an incision of about 5 cm or less, e.g., about 4 cm or less, about 3 cm or less, about 2 cm or less, about 1.5 cm or less, or about 1 cm or less, such as about 0.5 cm, about 1 cm, about 1.5 cm, about 2 cm, about 2.5 cm, about 3 cm, about 3.5 cm, about 4 cm, about 4.5 cm, or about 5 cm. For example, introducer 100 may be suitable for implantation of an implant into an incision having a length of between about 0.5 cm and about 5 cm, between about 1 cm and about 3 cm, or between about 1.5 cm and 3.5 cm.

In some embodiments, as described above, introducers disclosed herein (e.g., introducers 100, 100', 600, 700, or variations thereof) may be configured for use with different types of nozzles interchangeably. For example, handles (e.g., handle 120) may have attachment features complementary to different sizes, shapes, and/or types of nozzles. In such embodiments, nozzle shape, size, and/or type may therefore be selected for a given implant, procedure, and/or patient. Various characteristics of the nozzles disclosed herein (e.g., rigidity/flexibility of the materials defining the distal opening of the nozzle, the shape of the distal opening, the cross-sectional size of the distal opening, etc.) may allow the medical professional to better control the trajectory and/or speed at which the implant is delivered and/or allow for a more precise placement of the implant into the desired implantation site.

Figure 4B:
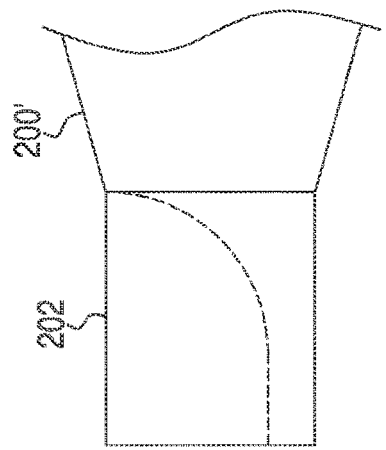
FIGS. 4A-4C show exemplary views of a distal tip of an introducer, according to some aspects of the present disclosure.
Figure 4C:
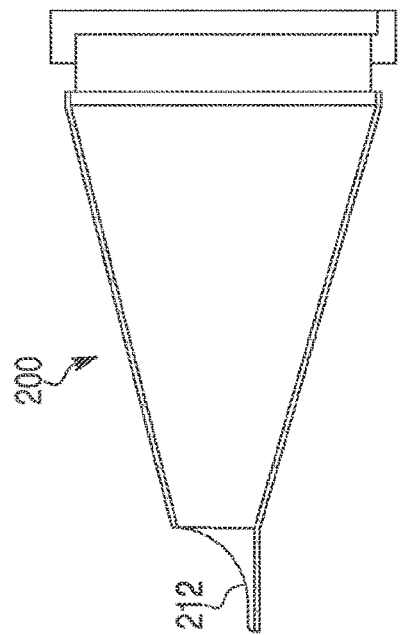
Figure 4A:
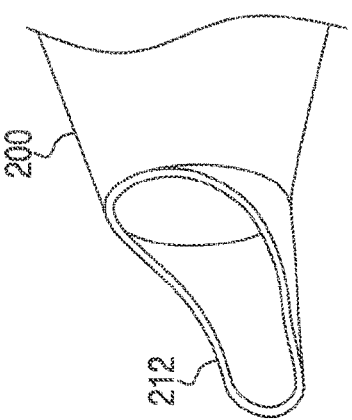

FIGS. 4A and 4C depict a conically-tapered nozzle 200, similar to nozzles 110, 110', having an asymmetrical tip. For example, nozzle includes an extension 212 adjacent to the distal opening of the nozzle. FIG. 4A depicts a perspective view of extension 212, and FIG. 4C depicts a side cross-sectional view of nozzle 200. Extension 212 may allow for more precise placement of the distal end of nozzle 200 into or at an incision site, and may guide expulsion of an implant through nozzle 200 into a desired position. FIG. 4B depicts how extension 212 may be cut from a solid cylindrical portion at an end of the nozzle, by, e.g., removal of section 202. Extension 212 need not be a separate component and may instead be an integral part of nozzle 200. In some embodiments, nozzle 200 and/or extension 212 may be made from or comprise a relatively rigid material (e.g., a relatively rigid polymer such as polypropylene, polycarbonate, polyurethane, polyetheretherketone (PEEK), or other rigid or semi-rigid plastic or polymer, or a biocompatible metal), so as to be able to precisely deliver an implant to a desired site. Moreover, extension 212, once inserted through an incision, may aid in keeping a relatively small incision open so that an implant may pass through the incision and into the desired site.

Figure 5:
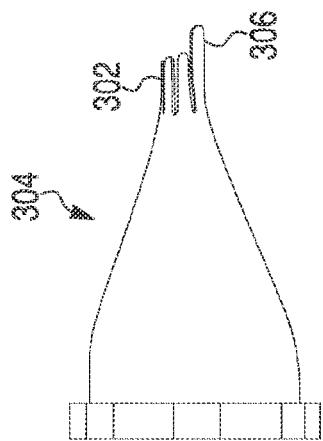
FIGS. 5, 6, 7A, and 7B show exemplary views of nozzles of introducers, according to some aspects of the present disclosure.
Figure 6:
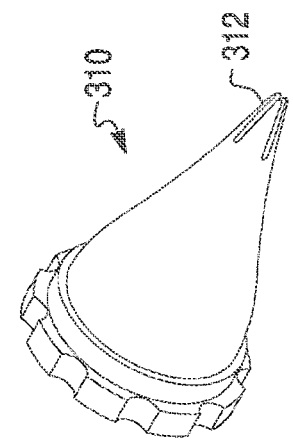

In some examples, the distal end of nozzles according to the present disclosure may be defined by or comprise two or more strips extending generally parallel to the longitudinal axis of the nozzle. Such strips may allow for the distal opening to widen as the strips flex radially outwards in response to a compressed implant passing through the distal opening. Such a configuration may help to avoid deformation of the implant during the implantation procedure. In some examples, one or more of the strips may extend farther than one or more of the other strips, e.g., to assist in guiding the implant into an incision site. Each strip may have the same or different amount of rigidity or flexibility than the other strips. For example, FIGS. 5 and 6 depict two tapering bulb-shaped nozzles 300, 304, having differing distal ends. Nozzle 300 includes strips 302 at the distal tip, extending in the distal direction. Strips 302 may facilitate placement of an implant into a relatively small incision, wherein strips 302 may separate (flex away from each other) as an implant passes through the distal end of nozzle 300. Thus, for example, strips 302 may flex radially outward such that the implant does not become over-compressed as it is expelled into a surgical site. Nozzle 304 includes one strip 306 longer than the rest of the strips 302, similar to extension 212 of nozzle 200. Extended strip 306 similarly may allow for more precise placement of the distal end of nozzle 304 into or at an incision site, and help to guide expulsion of the implant through nozzle 304 into the desired site. Nozzles 300, 304 may comprise any material suitable for other nozzles disclosed herein (e.g., nozzle 110). In some embodiments, nozzles 300, 304 may comprise a semi-rigid material (e.g., a semi-rigid plastic, silicone, or other polymer) that may allow for the strips to flex in response to pressure.

Figure 7A:
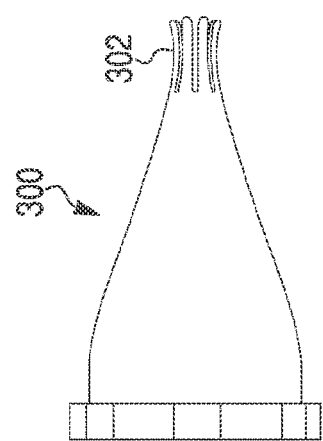
Figure 7B:
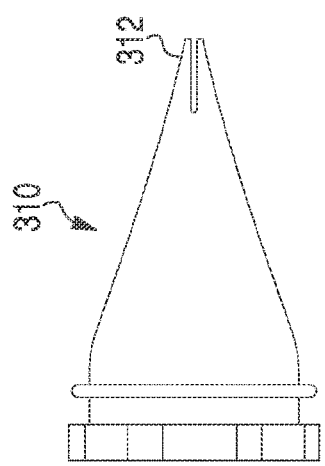

FIGS. 7A and 7B depict a conically-tapered nozzle 310 with a narrow opening at the distal end. The narrow opening is defined by strips 312, which may separate and flex radially outward as an implant passes through the opening. The narrowness of the opening may facilitate introduction of nozzle 310's distal end into a small incision (e.g., an incision less than 3 cm, e.g., 0.5 cm to 2.5 cm, or 2 cm or less). Nozzle 310 may comprise any material suitable for other nozzles disclosed herein (e.g., nozzle 110).

Figure 8:
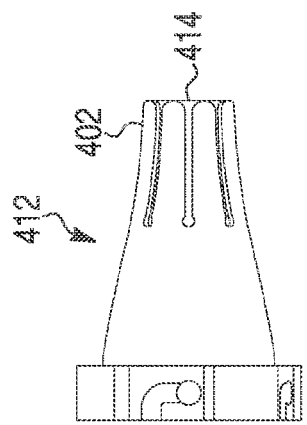
FIGS. 8-10 show exemplary views of further nozzles of introducers, according to some aspects of the present disclosure.
Figure 9:
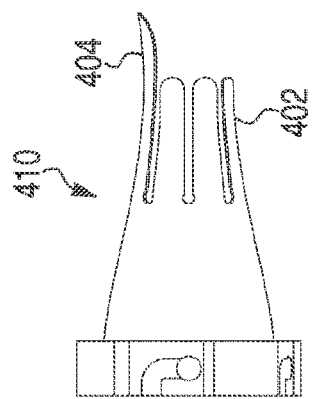

FIGS. 8 and 9, similar to FIGS. 5 and 6, depict tapered nozzles 400, 410 with distally-extending strips 402 that define the distal opening. As compared to nozzles 300, 304, nozzles 400, 410 have larger openings, which may allow for larger implants, or implants with less compressibility, to pass through. Nozzle 410, similar to nozzle 304, includes one strip 404 extending distally beyond the other strips 402. Strip 404 may facilitate placement of the distal end of nozzle 410 into or at an incision site, and may help to guide and/or control expulsion of an implant through nozzle 410 into a desired position. Nozzles 400, 410 may comprise any material suitable for other nozzles disclosed herein (e.g., nozzle 110).

Figure 10:
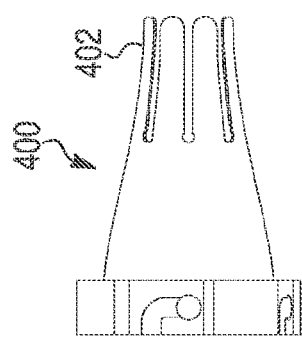

FIG. 10 depicts a conically-tapered nozzle 412 with distally-ending strips 402 defining the distal opening. The strips 402 may be covered or joined together by a flexible film 414 (e.g., an elastic silicone film) which may allow the strips 402 to separate or flex away from each other, while simultaneously preventing the strips 402 from splitting apart and piercing, scratching, and/or nicking patient tissue and/or an implant. The material of the film 414 may be the same or different than the material of the remainder of the nozzle 412. For example, the film 414 and the remainder of the nozzle may comprise the same type of polymer, wherein the film 414 has a thinner wall thickness that allows the film 414 to stretch.

Figure 11A:
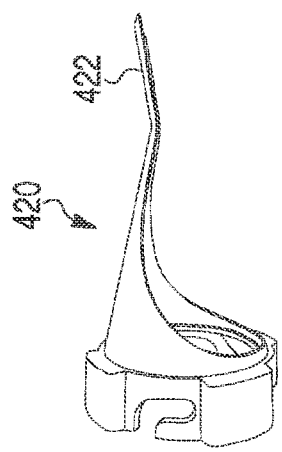
FIGS. 11A and 11B show an exemplary two-part nozzle, according to some aspects of the present disclosure.
Figure 11B:
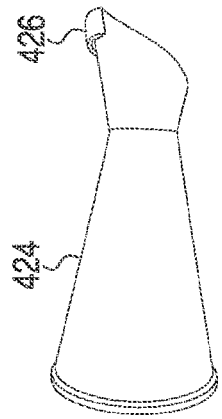
Figure 12A:
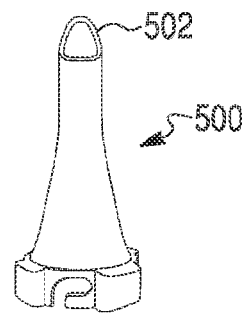
FIGS. 12A-12D show exemplary distal tip shapes of nozzles of introducers, according to some aspects of the present disclosure.
Figure 12B:
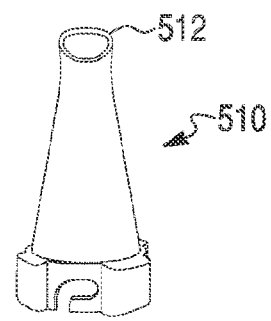
Figure 12C:
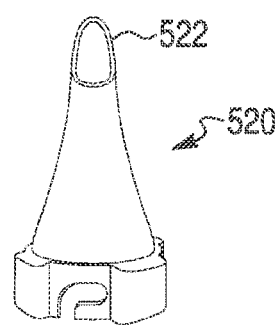
Figure 12D:
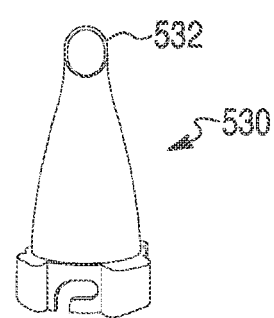
Figure 13:
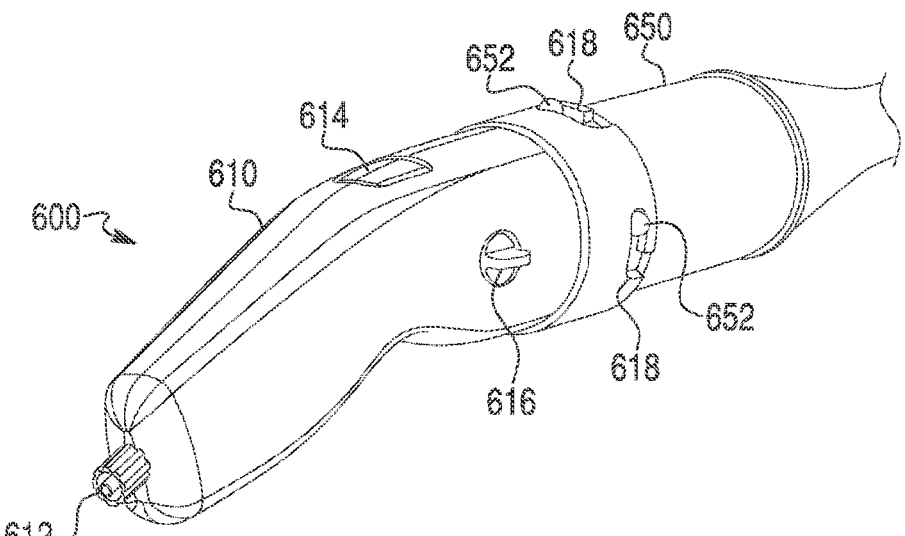
FIG. 13 shows a perspective view of a handle of an introducer, according to some aspects of the present disclosure.
Figure 14A:
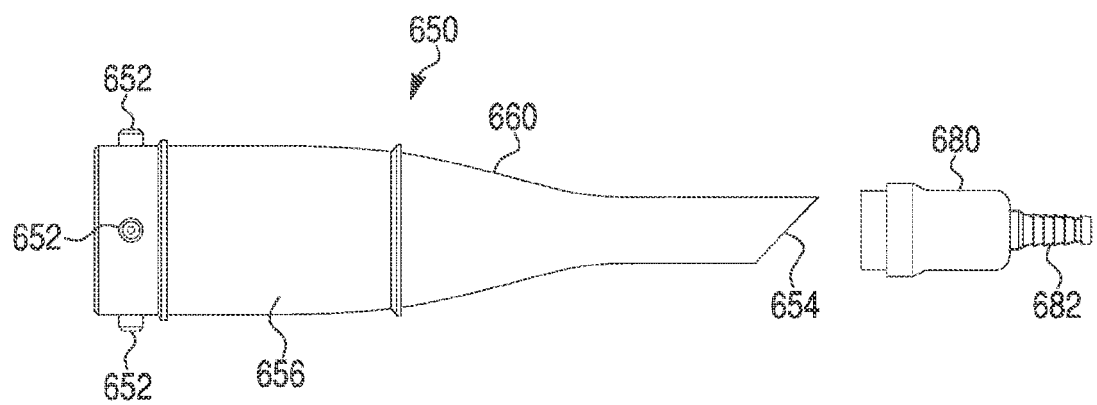
Figure 14B:
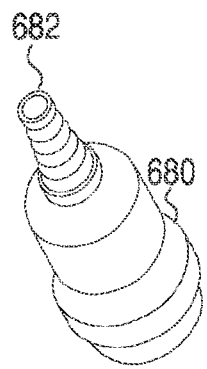
Figure 14C:
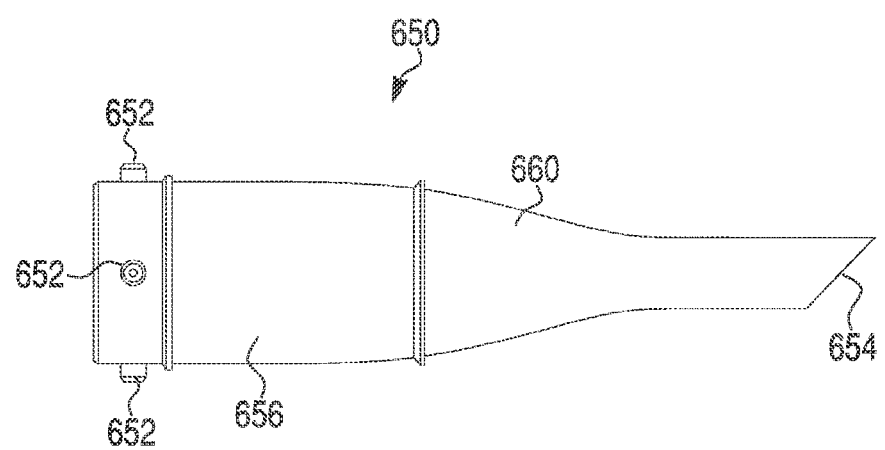

FIGS. 11A and 11B depict a two-part nozzle according to some aspects of the present disclosure. FIG. 11A depicts a first component 420 having a long extension 422 extending in the distal direction, adjacent to the distal opening. Component 420 may be relatively rigid and may comprise, e.g., a rigid or semi-rigid plastic or other polymer, or a biocompatible metal. FIG. 11B depicts a second component 424 having an inwardly-tapered shape, which arrives at a narrowest point proximate a middle portion of the second component 424 and then flares outward in the distal direction. A distal opening in the second component 424 may be angled, so as to form an angled opening. Component 424 may be more flexible than component 420. e.g., comprising a semi-rigid or flexible polymer, or any material suitable for other nozzles disclosed herein (e.g., nozzle 110). Components 420 and 424 may be configured to fit together for use. For example, component 424 may nest within component 420, wherein distal extension 422 of component 420 is received within a sleeve 426 of component 424. The first and second components 420, 424 may be affixed or otherwise coupled together to form the nozzle.

FIGS. 12A-12D depict further exemplary nozzles 500, 510, 520, 530 having different exemplary shapes of distal openings 502, 512, 522, 532, respectively. Thus, for example, the perimeter of the distal opening may be generally oval, oblong, trapezoidal, or may be asymmetrical in shape. These nozzles may comprise, e.g., any material suitable for other nozzles disclosed herein (e.g., nozzle 110). Each nozzle may be constructed or provided with a variety of distal opening sizes. For example, distal openings 502, 512, 522, 532 may each have a cross-sectional diameter ranging from about 20 mm to about 40 mm, such as about 24 mm, about 28 mm, or about 30 mm. For example, the maximum cross-sectional diameter may range from about 20 mm to about 40 mm, from about 30 mm to about 40 mm, from about 25 mm to about 35 mm, or from about 25 mm to about 30 mm.

FIGS. 13-17 depict views of an introducer 600 according to aspects of the present disclosure. Introducer 600 includes handle 610 and nozzle 650. Handle 610 (shown in FIGS. 13, 15, 16, and 17) includes fluid supply conduit 612, actuator 614, vent switch 616, and retention apertures 618. Nozzle 650 (shown in FIGS. 14A, 14C, 14D, 15, 16, and 17) includes a distal portion 660 having a distal opening 654, a middle portion 656, and a proximal end portion with mating elements, e.g., protrusions 652, complementary to the handle 610 as discussed below. Introducer 600 further includes a distal cap 680 having a distal cap nozzle 682.

Introducer 600, handle 610, and nozzle 650, and their parts (e.g., actuator 614, fluid supply conduit 612, distal opening 654, etc.) may share any characteristics, materials, functionality, etc. with, e.g., introducer 100, handle 120, and nozzle 110 and their parts, and as such, will not be described in repetitive detail. For example, distal opening 654 may have any size, shape, extensions, tabs, etc., described with respect to any other nozzle disclosed herein. Fluid supply conduit 612 may be coupled to any suitable source of fluid, as has been described previously with respect to fluid supply lumen 122. In some embodiments, distal portion 660 of nozzle 650 is elongated (e.g., as compared to nozzle 110), which may assist in guiding expulsion of an implant into a desired implantation site.

Middle portion 656 of nozzle 650 may define a cavity, and may be configured to be loaded with, and house, an implant in a radially compressed and/or elongated configuration for introduction into an implantation site. In some embodiments, as shown, the distal portion 660 of nozzle 650 may be more tapered (have a smaller cross-sectional dimension) than middle portion 656, such that an implant loaded into middle portion 656 is not as compressed as it would be in distal portion 660. In some embodiments, middle portion 656 may have an approximately equal diameter along its length. In some embodiments, for example, middle portion 656 may be generally cylindrical in shape. A proximal end portion of nozzle 650 may be open to allow for loading of an implant into the cavity defined by middle portion 656.

As shown in FIGS. 14A, 14B, 14D, and 16, distal cap 680 may be coupleable to nozzle 650, over distal opening 654, e.g., via friction fit or other complementary mating features. Distal cap 680 may be configured to form a seal around distal opening 654 to channel fluid through the distal cap nozzle 682 and prevent fluids from leaking or otherwise escaping other than through distal cap nozzle 682. Distal cap nozzle 682 may include a distal opening to which a vacuum may be applied. Application of a vacuum to distal opening 654 of the nozzle 650, via distal cap nozzle 682, may facilitate loading of an implant through the proximal end portion of nozzle 650 via suction. Once an implant is loaded into nozzle 650, or once an implantation site is ready to receive an implant, distal cap 680 may be removed from nozzle 682 such that distal opening 654 is exposed.

Figure 16:
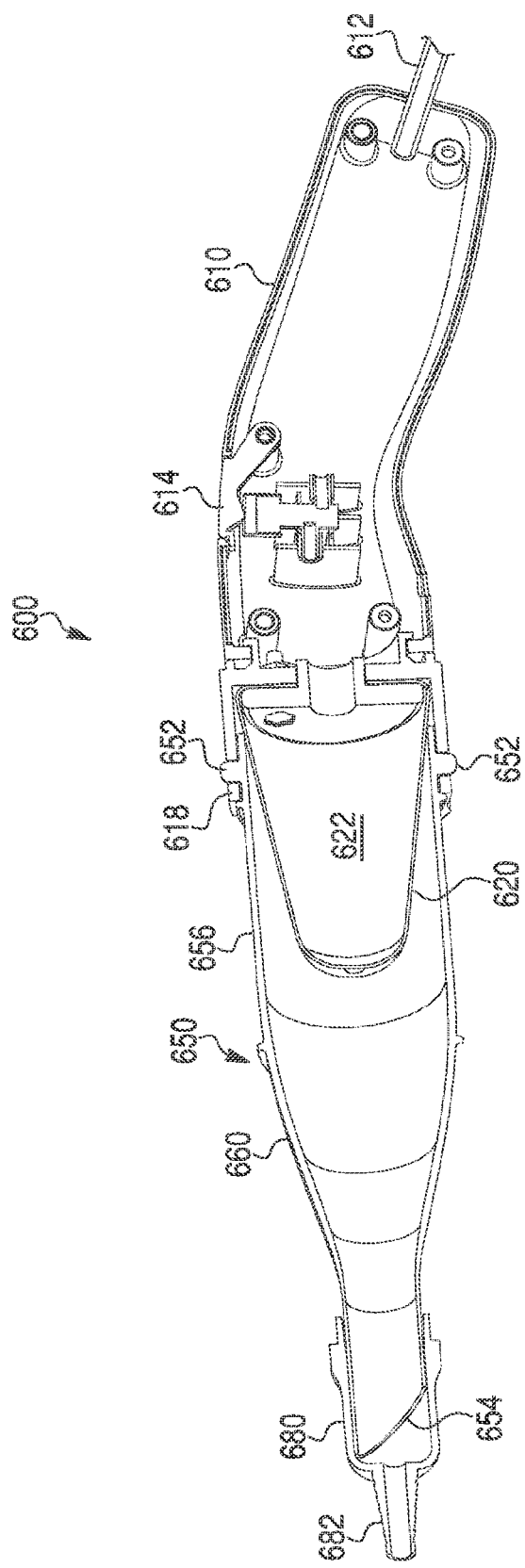
FIG. 16 shows a cross-sectional side view of an assembled introducer, according to some aspects of the present disclosure.
Figure 17:
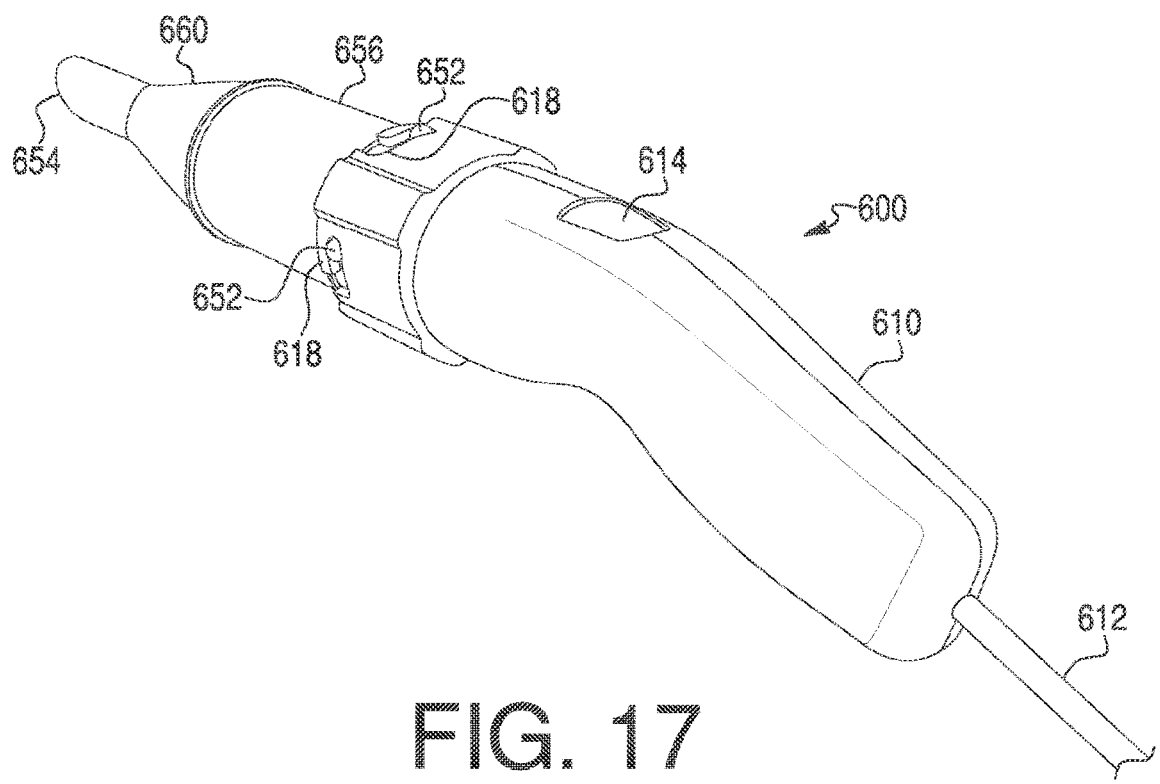
FIG. 17 shows a perspective view of the assembled introducer shown in FIGS. 15 and 16, according to some aspects of the present disclosure.

The proximal end portion of nozzle 650 may be coupled to a distal end of handle 610 (as shown in, e.g., FIG. 16). For example, the proximal end portion of the nozzle 650 may fit snugly within the distal end of the handle by sliding protrusions 652 proximally into channels defined by retention apertures 618 of the handle 610. Each protrusion 652 may slide into a circumferential portion of the channels defined by retention apertures 618 to secure nozzle 650 to handle 610. The channels optionally may have an L-shape, as shown, such that rotating the nozzle 650 relative to the handle 610 may lock the protrusions 652 within the channels. After nozzle 650 has been loaded with an implant, the nozzle 650 may be coupled to handle 610 in this manner to enclose the implant within the introducer 600. While FIGS. 13, 14A, 14C. 14D, and 15 depict the nozzle 650 with protrusions 652 and the handle 610 with channels that receive protrusions 652, in other examples, the nozzle 650 may include channels (see, e.g., FIGS. 12A-12D) that receive protrusions of the handle. Further, other complementary mating elements may be used to detachably secure the nozzle 650 to the handle 610.

As shown in FIG. 16, a flexible membrane 620 may be coupled to the handle 610, e.g., a distal portion of handle 610. In some embodiments, membrane 620 may be at least partially disposed within the cavity of middle portion 656, the membrane 620 defining a chamber 622 into which fluid may be received from fluid supply conduit 612. During operation of introducer 600, actuator 614 may be engaged to allow fluid to travel via fluid supply conduit 612 into chamber 622 defined by membrane 620. Actuator 614 may be a switch, button, lever, or connector that, when engaged, connects fluid supply conduit 612 to cavity 622. As fluid is received into chamber 622, membrane 620 may expand into the cavity of middle portion 656. Pressure from the fluid may push an implant disposed in cavity defined by middle portion 656 distally, through distal portion 660 of nozzle 650 and distal opening 654, and into a desired implantation site. In some embodiments, chamber 622 and/or membrane 620 may be expandable enough to fill a majority of an interior of nozzle 650, such that distal expansion of chamber 622 and distal movement of membrane 620 displaces an implant within nozzle 650 until it is expelled from introducer 600. In some embodiments, chamber 622 may be partly defined by membrane 620 and partly defined by, e.g., a distal end of handle 610, as opposed to being surrounded by membrane 620. Membrane 620 may be affixed securely to handle 610 to allow passage of fluid into chamber 622 without detachment of membrane 620 from handle 610.

Vent switch 616 may control a vent fluidly coupling an interior of chamber 622 with an exterior of introducer 600. According to some aspects, when vent switch 616 is closed, vent switch 616 prevents fluid from chamber 622 escaping. Further, for example, when actuated or opened, vent switch 616 may allow for fluid within chamber 622 to vent outside of introducer 600, thereby deflating or reducing fluid pressure within chamber 622 to an extent that chamber 622 is pressurized relative to an exterior of introducer 600. Vent switch 616 may operate mechanically or electronically. In some embodiments, for example, vent switch 616 may include a powered switch that may, e.g., activate suction, a fan, or a blower to actively remove fluid from within chamber 622. Vent switch 616 may thereby be used to stop or reduce expulsion pressure within nozzle 650. e.g., to stop or slow expulsion of an implant from nozzle 650, and/or to reset introducer 600 after an implant has been expelled from nozzle 650.

As has been described with respect to introducer 100, one or more parts of introducer 600 may be reusable (e.g., handle 610, distal cap 680, nozzle 650). For example, the material(s) that form various parts of introducer 600 may be capable of sterilization. One or more parts of introducer 600 may also or alternately be disposable, e.g., wherein the one or more parts of introducer 600 may be replaced with new, unused parts.

Figure 18:
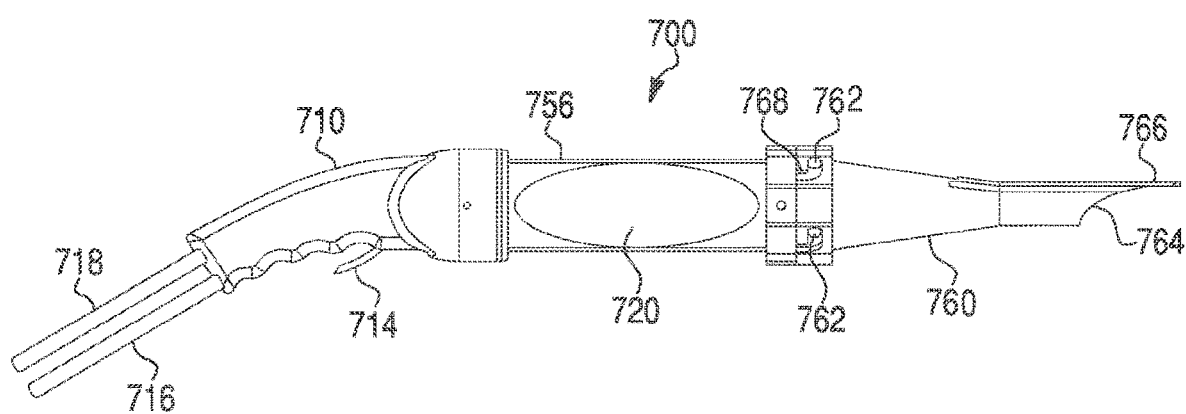
FIG. 18 shows a side view of another introducer, according to aspects of the present disclosure.

FIG. 18 depicts an introducer 700 loaded with an implant 720, the introducer 700 sharing some characteristics of introducer 600 and including different characteristics than introducer 600. For example, introducer 700 includes handle 710, actuator 714, fluid supply conduit 716, electrical supply conduit 718, a middle portion 756 defining a cavity in which implant 720 is disposed, a nozzle 760 affixed to middle portion 756 by extensions 762 on middle portion 756 slid into channels defined by retention apertures 768 of nozzle 760. Nozzle 760 includes distal opening 764 and distal extension 766.

Parts of introducer 700, such as, handle 710, actuator 714, fluid supply conduit 716, electrical supply conduit 718, middle portion 756 and nozzle 760 may share any characteristics, materials, functionality, etc. with, e.g., introducers 100, 100', 600, handles 120, 610, actuators 128, 614, fluid supply lumen 122, fluid supply conduit 612, and\or distal openings 112, 654, etc. As such, they will not be described in repetitive detail.

Middle portion 756 may be separate from, or separable (detachable) from, nozzle 760, in some embodiments. As shown with respect to introducer 700, middle portion 756 may be coupled separately to handle 710 and/or nozzle 760. Additionally or alternately, middle portion 756 may be apiece of (e.g., integrated with) handle 710. In such cases, implant 720 may be loaded through a distal opening of middle portion 756 before nozzle 760 is coupled to middle portion 756. Handle 710 may be equipped with a user-friendly grip. In some embodiments, actuator 714 is a rotatable trigger. Electrical supply conduit 718 may supply electrical power to one or more aspects of introducer 700. For example, in some embodiments, electrical supply conduit 718 may supply electrical power to a vacuum source disposed in handle 710 and/or middle portion 756, which may be used to create suction in, and load implant 720 into, middle portion 756.

Figure 19A:
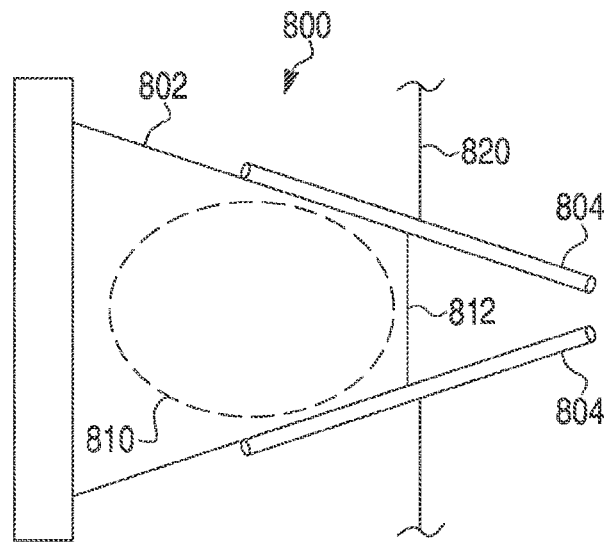
FIGS. 19A and 19B show side cross-sectional views of parts of another introducer, according to aspects of the present disclosure.
Figure 19B:
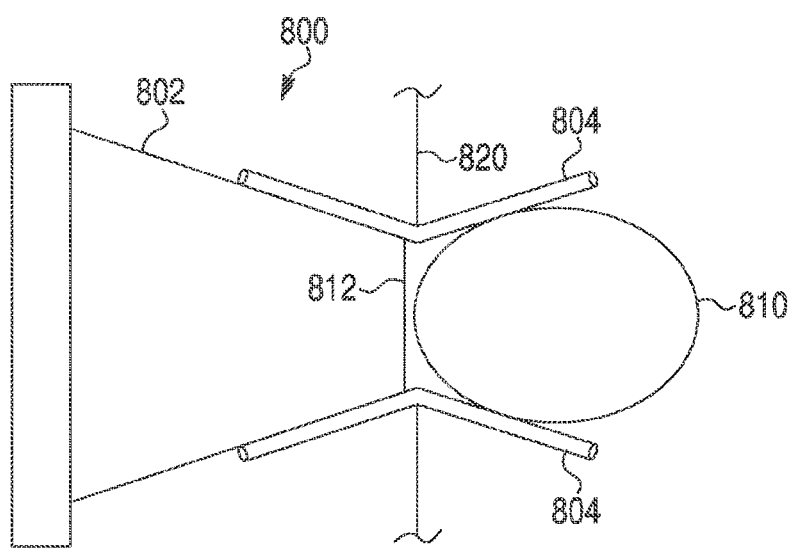

FIGS. 19A and 19B depict, in schematic form, a nozzle 800 holding and depositing an implant 810 through an incision in tissue 820. Nozzle 800 includes two flexible or semi-flexible strips 804, disposed on (or forming) at least two sides of a tapering portion 802. Strips 804 may be relatively more flexible than tapering portion 802, which may comprise a rigid or semi-rigid material. In some embodiments, tapering portion 802 may be relatively rigid at a proximal end, and semi-rigid (more flexible) at a distal end portion. Thus, for example, materials of different flexibility or the same material with different configurations that allow for variable flexibility, may be used in the tapering portion 802. Strips 804 may assist in positioning the nozzle 800 at or through the incision site. During expulsion or deployment of implant 810, strips 804 may flex or bend outward to widen distal opening 820, as shown in FIG. 19B. This flexibility may assist in guiding implant 810 through the incision and into an implantation site as the implant 810 expands free of the confines of tapering portion 802.

Figure 20:
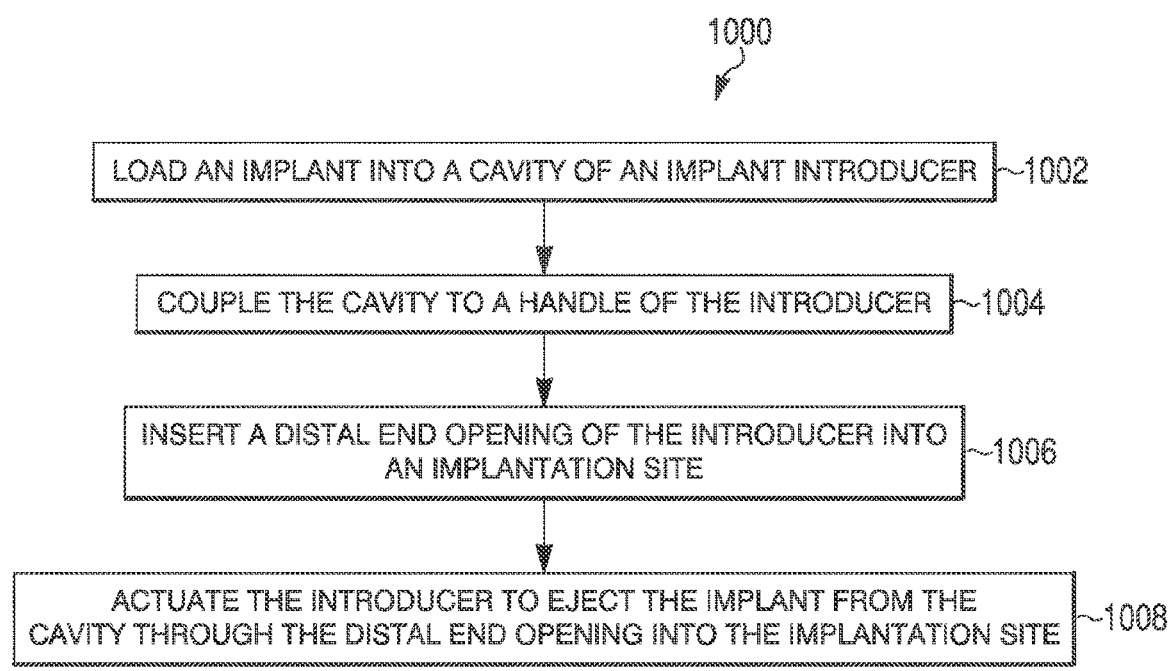
FIG. 20 shows a flow chart of steps in an exemplary method according to some aspects of the present disclosure.

As has been alluded to and described with respect to FIGS. 1-19B, methods of loading an implant into an introducer and delivering the implant to an implantation site, e.g., within patient tissue, are contemplated by the present disclosure. FIG. 20 depicts, in flow chart form, an exemplary method 1000 for loading an implant and delivering the implant to an implantation site. Method 1000, and variations thereof, may be applicable to any introducer described or encompassed by this disclosure, as well as other introducers. It will be contemplated by those of ordinary skill in the art that FIG. 20 depicts merely an exemplary method, of which many variations are possible. In some embodiments, one or more steps of FIG. 20 may be added, removed, duplicated, or performed out of order. The steps of method 1000, and variations thereon, may be performed by one or more users, such as medical professionals, technicians, assistants, etc.

According to step 1002 of method 1000, an implant may be loaded into a cavity of an implant introducer (e.g., a cavity defined by a nozzle, such as nozzles 110, 110', 650, 760. For example, a user having an assembled introducer (e.g., introducers 100, 100'. 600, 700, etc.) may first remove a nozzle (e.g., nozzle 110, 110', 650, 760) from a handle or other components of the introducer. Then, the implant may be loaded into. e.g., a proximal opening of the nozzle (e.g., a proximal opening of nozzle 110, 110', 650), or a distal opening of a cavity (e.g., the cavity defined by middle portion 756 of introducer 700).

In some aspects, the implant may be inserted into the nozzle or into a cavity of the introducer with the assistance of a sheath or other device suitable for compressing the implant. For example, the implant may be pre-loaded or inserted into an introducer sheath to facilitate the sterile loading of the implant into the nozzle, and/or to manipulate (e.g., compress, elongate, etc.) the implant toward the insertion configuration. In further aspects, a vacuum or suction may be used to load an implant into a cavity. For example, with respect to introducer 600 and variations thereof, distal cap 680 may be affixed over distal opening 654 of nozzle 650, e.g., to form a fluid-tight seal. A vacuum may be applied through the opening of distal cap nozzle 682 while an implant is placed at an open proximal end of nozzle 650. The reduction in pressure caused by the applied vacuum may draw the implant into the proximal opening of nozzle 650, into the cavity defined by middle portion 656 of nozzle 650.

According to step 1004, the cavity may be coupled to a handle of the introducer. For example, the nozzle may be coupled (e.g., affixed, reaffixed, clipped, screwed, etc.) to the handle body.

According to step 1006, a distal end opening of the introducer (e.g., distal opening 112, 112', 654, or 764) may be at least partially inserted into an incision of an implantation site. Depending on a location of the implantation site, the size of incision, the size (shape and volume) of the implant to be inserted, the length of the nozzle, etc., a larger or smaller fraction of the introducer may be inserted into the incision. In some embodiments, a distal tip of a nozzle may be inserted through an incision and at least partially into an implantation site.

According to step 1008, the introducer may be actuated to eject the implant from the cavity, through the distal end opening, and into the implantation site. An actuator (e.g., trigger, button, or other mechanism), such as actuator 128, 614, 714 may be engaged so as to allow a source of fluid (e.g., compressed air, liquid, etc.) to exert force on the implant, either directly or indirectly (e.g., through a membrane or balloon, such as membrane 620) in order to push, force, or otherwise expel the implant through the distal opening of the nozzle (e.g., distal opening 112, 112', 654, or 764), and into the implantation site via the incision (e.g., into a breast tissue pocket, gluteal tissue pocket, or other implantation site). In some aspects, retractors, such as those described in WO 2017/181144, incorporated herein by reference, may be used to ease expulsion of an implant and/or suitable placement of an implant into a surgical site, such as a desired portion of a patient's body (e.g., a breast pocket or other implantation site).

In embodiments where an actuator (e.g., trigger, button, or other mechanism) may be engaged so as to communicate with a source of fluid (e.g., compressed air or liquid) in order to inflate or expand an internal cavity, balloon, or diaphragm (e.g., cavity 622 depicted in FIG. 16) to push, force, or otherwise expel the implant through the distal opening of the nozzle, once the implant has been expelled, a release mechanism (e.g., vent switch 616, depicted in FIG. 13) may be employed to release fluid and deflate or contract the internal cavity, balloon, or diaphragm.

Appropriate expulsion pressures to expel an implant an introducer device according to the present disclosure may correlate to factors such as, e.g., (i) the volume/size/shape of the implant, (ii) the incision location and size, and/or (iii) the nozzle diameter. A chart may be provided to a medical professional or other user that defines these parameters for appropriate placement of the introducer device and the implant. The chart may be developed by bench and pre-clinical assessments, for example. In some embodiments, for example, a pressure of about 20 psi to about 100 psi may be suitable for expelling an implant, such as from about 20 psi to about 80 psi, from about 20 psi to about 60 psi, or from about 30 psi to about 50 psi, such as about 25 psi, about 30 psi, about 35 psi, about 40 psi, about 45 psi, about 50 psi, about 55 psi, about 60 psi, about 65 psi, about 70 psi, about 75 psi, about 80 psi, about 85 psi, about 90 psi, about 95 psi, or about 100 psi.

Additional aspects of preparing, loading, actuating, and using introducer devices, as well as aspects of calculating appropriate pressures and fluid volumes for loading and expelling implants from the introducer devices, are described in WO 2017/181144, incorporated by reference herein.

While principles of the present disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the present disclosure is not to be considered as limited by the foregoing description.

What is claimed is:

1. An implant introducer, comprising:
a handle;
a nozzle coupled to the handle, the nozzle having:
a cavity configured to receive an implant; and
a distal opening; and
a flexible membrane defining a chamber, wherein when the chamber receives a fluid, the flexible membrane expands into the cavity of the nozzle and pushes the implant through the distal opening of the nozzle.

2. The implant introducer of claim 1, further comprising a vent switch configured to vent the fluid from the chamber and deflate the flexible membrane.

3. The implant introducer of claim 1, wherein the flexible membrane is coupled to a distal portion of the handle.

4. The implant introducer of claim 1, wherein the handle further comprises:
a fluid supply conduit; and
an actuator configured to direct the fluid via the fluid supply conduit into the chamber defined by the flexible membrane.

5. The implant introducer of claim 4, wherein the fluid supply conduit is coupled to a fluid supply, the fluid supply comprising a portable compressed fluid canister, a pressurized gas line, or a pressurized water line.

6. The implant introducer of claim 4, wherein the actuator is located on an upper surface of the handle.

7. The implant introducer of claim 1, wherein a pressure of the fluid is from about 20 psi to about 60 psi.

8. The implant introducer of claim 7, wherein the pressure of the fluid is about 50 psi, about 55 psi, or about 60 psi.

9. An implant introducer, comprising:
a handle having a fluid supply conduit; and
a nozzle coupled to the handle, the nozzle having:
a cavity configured to receive an implant; and
a distal portion including a distal opening and an asymmetrical tip formed by an extension adjacent to the distal opening.

10. The implant introducer of claim 9, wherein the cavity of the nozzle is generally cylindrical in shape.

11. The implant introducer of claim 9, wherein the distal portion of the nozzle has a smaller cross-sectional dimension than the cavity of the nozzle.

12. The implant introducer of claim 11, wherein the cross-sectional dimension of the distal portion of the nozzle is from about 20 mm to about 40 mm.

13. The implant introducer of claim 12, wherein the cross-sectional dimension of the distal portion of the nozzle is from about 25 mm to about 30 mm.

14. The implant introducer of claim 9, wherein the distal portion of the nozzle is elongated to assist in guiding the implant into a desired implantation site.

15. The implant introducer of claim 9, wherein the nozzle further comprises a proximal end portion with mating elements complementary to the handle.

16. The implant introducer of claim 15, wherein the proximal end portion of the nozzle is open and configured to receive the implant during loading.

17. The implant introducer of claim 9, wherein the distal portion of the nozzle is more flexible than a proximal end portion of the nozzle.

18. The implant introducer of claim 9, wherein an inner surface of the nozzle comprises a water-activated lubricious coating.

19. The implant introducer of claim 11, wherein the cross-sectional dimension of the distal portion of the nozzle is from about 5 mm to about 50 mm.

20. The implant introducer of claim 9, wherein the implant is elastic and the nozzle is configured to compress the elastic implant.

21. The implant introducer of claim 9, wherein the extension is an integral part of the nozzle.

22. The implant introducer of claim 9, wherein the nozzle is constructed of a relatively rigid material.

23. The implant introducer of claim 22, wherein the relatively rigid material comprises polypropylene, polycarbonate, polyurethane, polyetheretherketone (PEEK), or a biocompatible metal.

24. An implant introducer, comprising:
a handle;
a nozzle coupled to the handle, the nozzle having:
a proximal end portion;
a cavity; and
a distal opening; and
a distal cap removably coupled to the distal opening of the nozzle, wherein the distal cap has:
a first configuration in which the distal cap is coupled to the distal opening of the nozzle, the distal cap having an opening to apply a vacuum to the distal opening of the nozzle and load an implant into the cavity of the nozzle through the proximal end portion of the nozzle via suction; and
a second configuration in which the distal cap is removed to expose the distal opening of the nozzle.

25. The implant introducer of claim 24, further comprising a flexible membrane defining a chamber, wherein when the chamber receives a fluid, the flexible membrane expands into the cavity of the nozzle and pushes the implant through the exposed distal opening of the nozzle in the second configuration.

26. The implant introducer of claim 24, wherein the nozzle further comprises an extension adjacent to the distal opening to form an asymmetrical tip.

* * * * *